United States Patent [19]

Egger

[11] Patent Number: Plant 7,439

[45] Date of Patent: Feb. 5, 1991

[54] VERBENA PLANT CALLED VERBENA "B"

[75] Inventor: Janet N. Egger, Ventura, Calif.

[73] Assignee: Mitsuwa Nursery, Inc., Moorpark, Calif.

[21] Appl. No.: 448,650

[22] Filed: Dec. 11, 1989

[51] Int. Cl.[5] ..... A01H 5/00

[52] U.S. Cl. ..... Plt./87

[58] Field of Search ..... Plt./88, 87

*Primary Examiner*—Howard J. Locker

*Attorney, Agent, or Firm*—Roylance, Abrams, Berdo & Goodman

[57] ABSTRACT

A perennial hybrid Verbena groundcover which is particularly distinguished by the deep rose red color of its flowers, a color which was not heretofore known to exist in Verbena groundcovers. In addition, the invention plant is floriferous and shares many desirable qualities enjoyed by its seed parent.

No Drawings

BACKGROUND TO THE INVENTION

The present invention relates to a new and distinct cultivar of Verbena plant botanically known as Verbena hybrid and named for patenting purposes as Verbena "B". Verbena "B" was developed by controlled breeding by crossing two commercial varieties, Verbena 'St. Paul' (seed parent) with *Verbena tenuisecta* 'Alba' (pollen parent).

BRIEF DESCRIPTION OF THE INVENTION

Verbena "B" is a perennial trailing groundcover with deep green leaves and floriferous, showy, deep rose red flowers that bloom from March to November in Southern California. The unique deep rose red color is believed to be a substantial step forward and an important advantage for Verbena "B" as compared to all other Verbena groundcovers.

DESCRIPTION OF THE DRAWING

The accompanying color photograph, forming a part of this disclosure, was taken in June, 1989 in a greenhouse in Moorpark, Calif., and shows a close-up of Verbena "B" growing in a nursery flat; the view being more or less straight down onto the plants. The photograph shows the typical flower and foliage forms and colors as true as are reasonably possible in this type of color photograph.

Comparison of Verbena "B" with its Seed Parent

The following characteristics distinguish Verbena "B" from its seed parent Verbena 'St. Paul' which is the only similar plant sold in the California groundcover industry. Its pollen parent, *Verbena tenuisecta* 'Alba' is a perennial groundcover with small white flowers and deeply dissected leaves and looks very different from Verbena "B".

In comparison to Verbena 'St. Paul', which is itself an excellent groundcover with large rose colored flowers, Verbena "B" is distinguished by its large deep rose red flowers and by its leaves which are less divided. Verbena "B" has larger flowers and broader flower spikes and its stems trail longer before branching. Verbena "B" has leaf margins that are botanically described as incised while Verbena 'St. Paul' has leaf margins that are cleft to parted. Verbena "B" and Verbena 'St. Paul' share many excellent traits. Both are extremely vigorous and spread rapidly to a width of one meter. They both have very prostrate habits of growth, long bloom seasons, and good frost tolerance. Both bloom profusely and provide abundant color.

The primary distinguishing characteristic of Verbena "B" is its deep rose red color. This color is new to Verbena groundcovers. That is, to the inventor's knowledge, Verbena "B" is the first Verbena groundcover having flowers of this color. It is believed that its unique deep rose red color contributes substantially to the commercial success of Verbena "B".

DETAILED DESCRIPTION

The following is a detailed description of Verbena "B" based on plants produced under commercial practices outdoors at Mitsuwa Nursery, Inc. in Moorpark, Calif. Color references are made to The Royal Horticultural Society Colour Chart, except where the context indicates a term having its ordinary dictionary meaning.

Parentage: A controlled cross of Verbena 'St. Paul' as the seed parent and *Verbena tenuisecta* 'Alba' as the pollen parent.

Propagation: Asexual reproduction by stem cuttings has shown that the unique features of the invention plant Verbena "B" are stable and true to type in successive propagations. Verbena "B" roots rapidly under warm conditions due to its vigor and roots adventitiously at every node.

Plant form: Plants are a vigorous growing, trailing groundcover.

Habit of growth: Plants are decumbent, spreading rapidly to approximately one meter in diameter under good growing conditions. Plants form a dense carpet to approximately 15 cm in height.

Stems: Stems are slender, 4-angled, appear wine colored in the sun and green in the shade, and are covered with hirsute hairs.

Foliage: Foliage is a rich green with simple, opposite leaves.

(1) *Leaf size.*—15-60 mm in length.
(2) *Leaf shape.*—Deltoid.
(3) *Leaf base.*—Truncate.
(4) *Leaf apex.*—Acute.
(5) *Leaf texture.*—Covered with moderately dense white strigose hairs.
(6) *Leaf margin.*—Incised with bottom two veins slightly cleft.

(7) *Color.*—Young foliage, top side — 147 A. Young foliage, underside — 137 C. Mature foliage, top side — 147 A. Mature foliage, underside — 147 B.

Flowering description:

(1) *Habit.*—Terminal spikes on ascending peduncles which are dense and fairly flat. Flowers on each spike continue to open for several weeks. Each spike has approximately 40 flowers. Plants are very free flowering.

(2) *Season of bloom.*—Varies with climate. In Moorpark, Calif. Verbena "B" flowers from March to November.

(3) *Flowers.*—Sessile on terminal spikes which are compact when young, and do not elongate when mature. Each flower has a subtending lanceolate-subulate bract with strigose hairs.

(4) *Flower parts.*—(a) Salverform corolla tube is straight and approximately 20 mm long with limbs spreading to 20 mm in diameter. (b) Calyx is tubular, sparsely glandular, with white strigose hairs and short teeth. It is more than half as long as the corolla tube and more than twice as long as the bract. (c) Stamens: four, in pairs, and sterile.

(5) *Color of petals.*—Young flowers, upside — 46 A-B. Mature flowers, upside — 60 A-B; downside, edges — 58 A; downside, middle — 63 C.

Disease resistance: No disease problem noted. Verbena "B" requires no fungicide drenching when grown under the propagation conditions of high heat and humidity, as are found in Moorpark, Calif.

I claim:

1. A new and distinct cultivar of Verbena plant as described and illustrated, particularly characterized by its floriferous showy deep rose red flowers, deep green foliage, vigorous growth, and trailing habit.

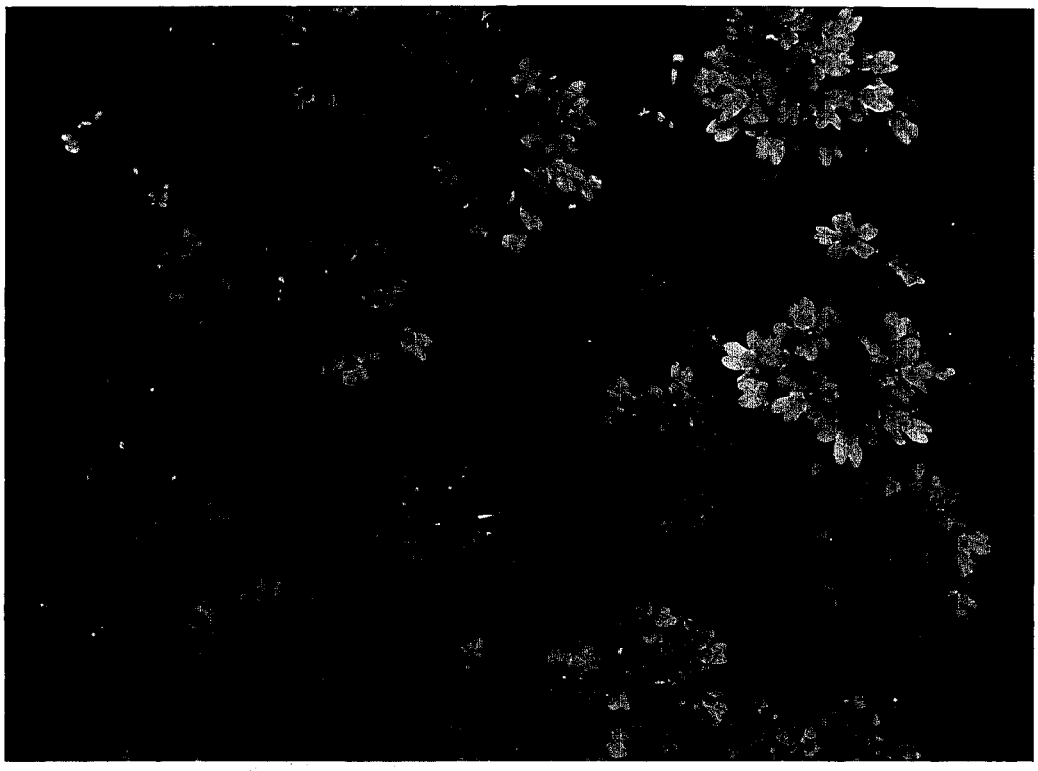

* * * * *